United States Patent
Gao et al.

(10) Patent No.: US 11,008,281 B2
(45) Date of Patent: May 18, 2021

(54) LOW-POLLUTION ANTIDEGRADANT COMPOUND AND ANTIDEGRADANT COMPOSITION AND RUBBER COMPOSITION COMPRISING THE SAME FOR TIRES

(71) Applicant: Sennics Co., Ltd., Shanghai (CN)

(72) Inventors: Yang Gao, Shanghai (CN); Hui Li, Shanghai (CN)

(73) Assignee: Sennics Co., Ltd., Shanghai (CN)

( * ) Notice: Subject to any disclaimer, the term of this patent is extended or adjusted under 35 U.S.C. 154(b) by 0 days.

(21) Appl. No.: 16/721,894

(22) Filed: Dec. 19, 2019

(65) Prior Publication Data
US 2020/0392069 A1     Dec. 17, 2020

(30) Foreign Application Priority Data
Jun. 14, 2019  (CN) .......................... 201910516287.6

(51) Int. Cl.
  *C07C 211/55*  (2006.01)
  *B60C 1/00*    (2006.01)
  *C08L 21/00*   (2006.01)

(52) U.S. Cl.
  CPC .............. *C07C 211/55* (2013.01); *B60C 1/00* (2013.01); *C08L 21/00* (2013.01); *C08L 2201/08* (2013.01)

(58) Field of Classification Search
  None
  See application file for complete search history.

(56) References Cited

U.S. PATENT DOCUMENTS

| | | | | |
|---|---|---|---|---|
| 3,432,460 A | * | 3/1969 | Spacht | C08K 5/18 524/255 |
| 4,647,328 A | * | 3/1987 | Rhee | B29D 30/52 156/128.1 |
| 2018/0237376 A1 | | 8/2018 | Guo et al. | |

FOREIGN PATENT DOCUMENTS

CN          106608827 A       5/2017

* cited by examiner

*Primary Examiner* — Clinton A Brooks
(74) *Attorney, Agent, or Firm* — Mei & Mark LLP; Manni Li

(57) ABSTRACT

Antidegradant compound of Formula I:

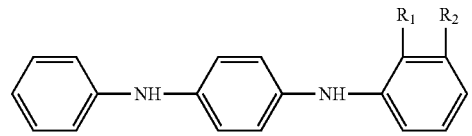

and antidegradant composition comprising the same and rubber composition comprising the antidegradant compound or composition. The rubber composition has good resistance to appearance discoloration while maintaining the mechanical and anti-aging properties, thus, are suitable for making the entire tire or as part of the rubber matrix.

21 Claims, No Drawings

LOW-POLLUTION ANTIDEGRADANT COMPOUND AND ANTIDEGRADANT COMPOSITION AND RUBBER COMPOSITION COMPRISING THE SAME FOR TIRES

CROSS-REFERENCE TO RELATED APPLICATION

The subject application claims priority on Chinese patent application no. CN201910516287.6 filed on Jun. 14, 2019 in China. The contents and subject matter of the Chinese priority application is incorporated herein by reference.

TECHNICAL FIELD

The present invention relates to rubber chemicals, particularly, antidegradant compounds and compositions as well as rubber composition comprising the same, which are useful for preparing rubber materials such as tires.

BACKGROUND ART

More than 200 types of rubber additives are currently in use, 50% of which are antidegradants; thus, antidegradants are the most important rubber additives in the world. N-1,3-dimethylbutyl-N'-phenyl-p-phenylenediamine (6PPD) is one of the antidegradants that are widely used in tire treads, tire sidewalls, hoses, cables, and seals, as it provides comprehensive protection for rubber, including strong ozone and flex resistance and inhibitory effects towards heat, oxygen, and harmful metals (such as copper), making the rubber products resistant to degradation catalyzed by copper and other heavy metals.

When a tire is exposed to environmental light, high temperature, and ozone for a long period of time or suffers from chemical corrosion, the tread and side of the tire show some discoloration due to aging of the rubber material, thereby affecting the overall appearance of the vehicle tire. Currently, most tires sold on the market are black; as the rubber raw material do not normally affect the black color in the rubber products, discoloration is less of a concern for producing these rubber products such as tires in black.

Pollution and discoloration caused by the antidegradants are the most serious among all types of rubber additives in rubber raw materials. Some antidegradants have coloring and polluting effects on the rubber; some antidegradants migrate in the rubber and pollute materials in contact therewith; and some antidegradants cause discoloration in the rubber products during long-term storage, especially under the light. These antidegradants, including the pollution-type antidegradants (such as 4010, 6PPD, IPPD, etc.), are not suitable for producing white and colored products. In some tires with high requirements for the appearance, phenolic antioxidants or saturated rubbers are used to reduce the amount of antidegradants and thus discoloration of the tires. Although the use of the phenolic antioxidants may reduce the discoloration of the tires, the anti-aging effect is not as good as the p-phenylenediamine antidegradants and causes great decrease in heat-oxygen resistance, ozone resistance, and flex resistance in tires. Further, although saturated rubbers such as EPDM may be used in tires to reduce the amount of antidegradants to certain degree, or even avoid use of antidegradants at all, to significantly improve the appearance of the tires, it is relatively expensive so the production cost is greatly increased while its low viscosity causes problems in the adhesion and molding of the tires.

In the current technology, 6PPD is used in a large amount to improve the static anti-aging property of the rubber articles. As 6PPD is a pollution-type antidegradant and can easily migrate to the surface of the rubber articles, it causes discoloration of rubber articles. However, a non pollution-type antidegradant that may replace 6PPD in all aspects has not yet been developed.

SUMMARY OF INVENTION

The present invention provides a novel low-pollution type antidegradant that improves the resistance to discoloration in the appearance of the rubber articles while maintaining their mechanical and anti-aging properties. Specifically, the present invention provides a compound of Formula I having the following structure:

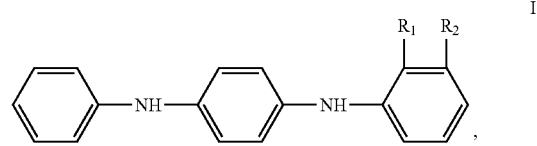

wherein $R_1$ and $R_2$ are identical or different, each being independently selected from C1-C12 alkyl and C3-C8 cycloalkyl, except that $R_1$ and $R_2$ are not methyl groups at the same time.

In the compound of formula I of the present invention, $R_1$ may be C1-C6 alkyl or C3-C6 cycloalkyl, and preferably, methyl, ethyl, isobutyl, or cyclohexyl.

In the compound of formula I of the present invention, $R_2$ may be C1-C12 alkyl or C3-C6 cycloalkyl, and preferably, methyl, ethyl, 1,3-dimethylbutyl, 1,4-dimethylamyl, octyl, 1-methyl-6-ethyloctyl, or cyclohexyl.

In the present invention, the compound of Formula I may have the following structure: when $R_1$ is methyl, $R_2$ is ethyl, 1,3-dimethylbutyl, or 1-methyl-6-ethyloctyl; or when $R_1$ is ethyl, $R_2$ is 1,4-dimethylamyl or cyclohexyl; or when $R_1$ is isobutyl, $R_2$ is cyclohexyl; or when $R_1$ is cyclohexyl, $R_2$ is octyl.

The present invention further provides an antidegradant composition comprising the compound of Formula I and at least one additional antidegradant that is not the compound of Formula I. The compound of Formula I has the following structure:

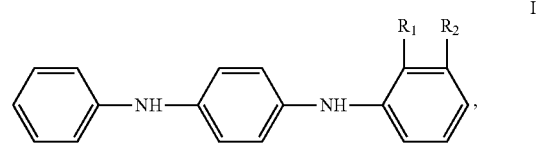

wherein $R_1$ and $R_2$ are identical or different, each being independently selected from C1-C12 alkyl and C3-C8 cycloalkyl.

In the antidegradant composition of the present invention, $R_1$ may be C1-C6 alkyl or C3-C6 cycloalkyl, and preferably, methyl, ethyl, isobutyl, or cyclohexyl.

In the antidegradant composition of the present invention, $R_2$ may be C1-C12 alkyl or C3-C6 cycloalkyl, and preferably, methyl, ethyl, 1,3-dimethylbutyl, 1,4-dimethylamyl, octyl, 1-methyl-6-ethyloctyl, or cyclohexyl.

In the antidegradant composition of the present invention, the compound of Formula I may have the following structure: $R_1$ and $R_2$ are both methyl; or when $R_1$ is methyl, $R_2$ is ethyl, 1,3-dimethylbutyl, or 1-methyl-6-ethyloctyl; or when $R_1$ is ethyl, $R_2$ is 1,4-dimethylamyl or cyclohexyl; or when $R_1$ is isobutyl, and $R_2$ is cyclohexyl; or when $R_1$ is cyclohexyl, $R_2$ is octyl.

In the antidegradant composition of the present invention, the additional antidegradant is a pollution-type antidegradant. Preferably, the additional antidegradant is 6PPD, IPPD, or both.

In the antidegradant composition of the present invention, the mass ratio of the compound of Formula I to the additional antidegradant is 1:6 to 6:1, and preferably 1:5 to 5:1.

In the antidegradant composition of the present invention, the antidegradant composition comprises the compound of Formula I of the present invention and at least one pollution-type antidegradant, and preferably, 6PPD, IPPD, or both.

In the antidegradant composition of the present invention, the antidegradant composition comprises the compound of Formula I wherein $R_1$ and $R_2$ may both be methyl, and the additional antidegradant is one or more pollution-type antidegradants, such as 6PPD, IPPD, or both.

The present invention further provides a rubber composition comprising the compound of Formula I of the present invention or the composition of the present invention. Preferably, in the rubber composition of the present invention, the antidegradant has an amount of 0.5-5.0 parts by mass, preferably 0.5-3.5 parts by mass, based on the amount of the diene elastomer in the rubber composition as 100 parts by mass.

The present invention further provides a rubber article that is prepared by using the rubber composition of the present invention as the rubber ingredient. Preferably, the rubber article is a tire, a rubber overshoe, a sealing strip, an acoustic panel, or a crash pad.

The present invention further provides a method for using the rubber composition of the present invention for preparing the rubber articles or retreading tires.

The present invention further provides a method for using the compound of Formula I for promoting resistance of a rubber or a rubber article to discoloration of the appearance or a method for preparing an antidegradant for promoting resistance of a rubber or a rubber article to discoloration of the appearance. The compound of Formula I has the following structure:

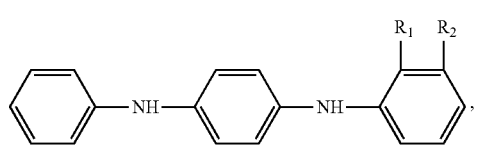

wherein $R_1$ and $R_2$ are identical or different, each being independently selected from C1-C12 alkyl and C3-C8 cycloalkyl.

In the method for using the antidegradant composition of the present invention, $R_1$ may be C1-C6 alkyl or C3-C6 cycloalkyl, and preferably, methyl, ethyl, isobutyl, or cyclohexyl.

In the method for using the antidegradant composition of the present invention, $R_2$ may be C1-C12 alkyl or C3-C6 cycloalkyl, and preferably, methyl, ethyl, 1,3-dimethylbutyl, 1,4-dimethylamyl, octyl, 1-methyl-6-ethyloctyl or cyclohexyl.

In the method for using the antidegradant composition of the present invention, the compound of Formula I may have the following structures: $R_1$ and $R_2$ are both methyl; or when $R_1$ is methyl, $R_2$ is ethyl, 1,3-dimethylbutyl, or 1-methyl-6-ethyloctyl; or when $R_1$ is ethyl, $R_2$ is 1,4-dimethylamyl or cyclohexyl; or when $R_1$ is isobutyl, $R_2$ is cyclohexyl; or when $R_1$ is cyclohexyl, $R_2$ is octyl.

DETAILED DESCRIPTION OF INVENTION

The present invention is further explained in the following detailed description. One of ordinary skill in the art may modify the invention as described therein without departing from the scope of the present invention.

The antidegradant of the present invention is N-phenyl-N'-disubstituted phenyl-p-phenylenediamine having a structure shown by the following Formula I:

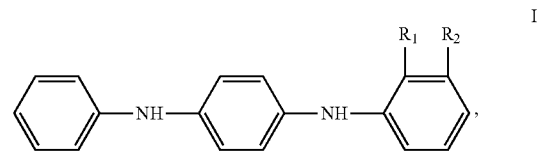

wherein $R_1$ and $R_2$ are identical or different, each being independently selected from C1-C12 alkyl and C3-C8 cycloalkyl.

In the present invention, a pollution-type antidegradant refers to the antidegradants that cause discoloration in the appearance when used in rubber products. Examples of the pollution-type antidegradants include, but not limited to, N-isopropyl-N'-phenyl-p-phenylenediamine (IPPD), N-1,3-dimethylbutyl-N'-phenyl-p-phenylenediamine (6PPD), and N-cyclohexyl-N'-phenyl-p-phenylenediamine (4010). A non-pollution-type antidegradant refers to the antidegradants that do not cause discoloration in the appearance when used in rubber products. Examples of the non-pollution-type antidegradants include, but not limited to, 2,6-di-tert-butyl-p-cresol (also known as antioxidant 264 or antioxidant BHT). A low-pollution-type antidegradant refers to the antidegradants that cause some degree of discoloration in the appearance which degree varies between the pollution- and non-pollution-type antidegradants and usually closer to the non-pollution-type antidegradants. Examples of the low-pollution type antidegradants include, but not limited to, 2,2,4-trimethyl-1,2-dihydroquinoline (also known as TMQ or RD).

In the present invention, "alkyl" may be a linear or branched alkyl. The alkyl has a length of 1-12 carbon atoms. In some embodiments of the present invention, the alkyl is C1-C6 linear or branched alkyl. Examples of the alkyl include, but are not limited to, methyl, ethyl, n-butyl, isobutyl, 1,3-dimethylbutyl, 1,4-dimethylamyl, octyl, 1-methyl-6-ethyloctyl, and 2,4,6-trimethyloctyl.

In the present invention, "cycloalkyl" means a cyclic alkyl group forming a ring. The number of the carbon atoms on the ring is usually 3-8. Examples of the cycloalkyl include cyclobutyl, cycloamyl, and cyclohexyl.

In some preferable embodiments, $R_1$ is a C1-C8 alkyl or a C3-C6 cycloalkyl, preferably C1-C6 alkyl or C3-C6 cycloalkyl, and more preferably, methyl, ethyl, isobutyl, or cyclohexyl.

In some preferable embodiments, $R_2$ is a C1-C12 alkyl or a C3-C6 cycloalkyl, and preferably, methyl, ethyl, 1,3-dimethylbutyl, 1,4-dimethylamyl, octyl, 1-methyl-6-ethyloctyl, or cyclohexyl.

In the compound of the present invention, the compound of Formula I may not include the compound wherein $R_1$ and $R_2$ are both methyl.

The antidegradant of the present invention improves the resistance to appearance discoloration while maintaining the excellent resistance to aging and mechanical property in the rubber articles, so it may be used alone or together with other known antidegradants as antidegradant composition for preparing rubber articles.

When the antidegradant of the present invention is added to a rubber composition as the sole antidegradant, the amount of the antidegradant is usually 0.5-5.0 parts by mass, preferably 0.5-3.5 parts by mass, more preferably 0.5-3.0 parts by mass, based on 100 parts by mass of the diene elastomer. For example, in some embodiments, the compound of Formula I with both $R_1$ and $R_2$ being methyl is added to a rubber composition as the only antidegradant and its amount is at 0.5-5.0 parts by mass, preferably 0.5-3.5 parts by mass, and more preferably 0.5-3.0 parts by mass, based on 100 parts by mass of the diene elastomer.

Further, the present invention provides an antidegradant composition comprising the antidegradant compound of the present invention. Optionally, the antidegradant composition of the present invention further comprises one or more additional antidegradants that is not the antidegradant compound of Formula I. Additional antidegradants suitable for use in the present invention may be known p-phenylenediamine antidegradants, for examples, N,N'-bis-(1,4-dimethylamyl)-p-phenylenediamine (77PD), N-isopropyl-N'-phenyl-p-phenylenediamine (IPPD), N-1,3-dimethylbutyl-N'-phenyl-p-phenylenediamine (6PPD), N-cyclohexyl-N'-phenyl-p-phenylenediamine (4010), a mixture of diphenyl, ditolyl, and phenyl tolyl p-phenylenediamine (3100), or combinations thereof. In some embodiments, the antidegradant composition of the present invention comprises the compound of Formula I wherein $R_1$ and $R_2$ are both methyl and optional additional antidegradants are as described above.

The antidegradant of the present invention has excellent resistance to appearance discoloration. In some embodiments of the present invention, the antidegradant composition also comprises known pollution-type antidegradants in addition to the antidegradant compound of the present invention, which include but are not limited to those like amines, aldehyde amines, and ketone amines. Adding appropriate amount of the antidegradant of the present invention to the pollution-type antidegradants can not only reduce the amount of the pollution-type antidegradants without prejudice to the mechanical and anti-aging properties of rubber, but also greatly improve the resistance of the rubber to appearance discoloration. In some embodiments, the pollution-type antidegradant is 6PPD, IPPD, or both. Further, in some embodiments, the antidegradant composition comprises the compound of Formula I wherein $R_1$ and $R_2$ are both methyl and pollution-type antidegradants (such as 6PPD, IPPD, or both).

The additional antidegradants may be added to the antidegradant composition of the present invention in an amount that is conventionally known, for examples, the amount of the additional antidegradant may be 0.1-5 parts by mass, 0.3-3.0 parts by mass, 0.3-2.5 parts by mass, 0.5-3.0 parts by mass, 0.5-2.5 parts by mass, or 0.5-2.0 parts by mass, based on 100 parts by mass of the diene elastomer, in the antidegradant composition of the present invention. Preferably, when an antidegradant composition of the present invention comprises one or more additional antidegradants, the total amount of the additional antidegradants is lower than the amount that is conventionally known, for examples, the total amount of the additional antidegradants may be in the range of 0.3-2.0 parts by mass, 0.5-2.0 parts by mass, 0.3-1.5 parts by mass, 0.5-1.5 parts by mass, or 1.0-1.5 parts by mass, based on 100 parts by mass of a diene elastomer.

In some embodiments, the antidegradant composition of the present invention comprises the antidegradant of the present invention and an additional antidegradant, or the antidegradant composition consists of the antidegradant of the present invention and the additional antidegradant. In these embodiments, the antidegradant of the present invention and the additional antidegradant may have a mass ratio of 1:6 to 6:1, preferably 1:5 to 5:1, and more preferably 1:1 to 5:1. For example, the antidegradant composition of the present invention may comprise the compound of Formula I wherein $R_1$ and $R_2$ are both methyl groups and the additional antidegradant, or consists of the compound of Formula I wherein $R_1$ and $R_2$ are both methyl groups and the additional antidegradant, wherein the compound of Formula I wherein $R_1$ and $R_2$ are both methyl groups and the additional antidegradant may have a mass ratio of 1:6 to 6:1, preferably 1:5 to 5:1, and more preferably, 1:1 to 5:1.

When the antidegradant composition of the present invention is added to a rubber composition as the antidegradant, the antidegradant composition generally is present in an amount of 0.5-5 parts by mass, for examples, 0.5-3.5 parts by mass, 0.5-3.0 parts by mass, 1.0-3.5 parts by mass, 1.0-3.0 parts by mass, 2.0-3.5 parts by mass, or 2.0-3.0 parts by mass, base on 100 parts by mass of a diene elastomer.

The antidegradant of the present invention can provide not only better long-term resistance to thermal aging and ozone aging but also superior resistance to appearance discoloration for a rubber composition. Therefore, the present invention further provides a rubber composition comprising the antidegradant of the present invention or the antidegradant composition of the present invention. For example, the rubber composition of the present invention may be a rubber composition comprising a compound of Formula I wherein $R_1$ and $R_2$ are both methyl groups and optional additional antidegradants. The amount of the antidegradant or the antidegradant composition in the rubber composition is as described above. Generally, the rubber composition may further comprise a diene elastomer, a reinforcing filler, and a crosslinker.

A diene elastomer refers to an elastomer with its monomers comprising dienes, and examples of a diene elastomer includes butadiene and isoprene. Diene elastomers suitable for use in the present invention may be various known diene elastomers in the field including but not limited to natural rubber (NR), butadiene rubber (BR), isoprene rubber, styrene butadiene rubber (SBR), chloroprene rubber (CR), nitrile butadiene rubber (NBR), isoprene/butadiene copolymer, isoprene/styrene copolymer, isoprene/butadiene/styrene copolymer, etc. In some embodiments of the rubber composition of the present invention, the diene elastomer consists of a natural rubber (such as SCR5) and a butadiene rubber (such as BR9000), and the mass ratio of the natural rubber to the butadiene rubber is in the range of 1:9 to 9:1, for examples, 2:8 to 8:2, 3:7 to 7:3, 4:6 to 6:4, or 1:1.

The antidegradant compound and composition of the present invention is useful not only in the diene elastomer based rubber composition but also in other types of elastomers such as non-diene elastomers and thermoplastic elastomers. One of skilled in the art would be able to adjust the amount of the compound or composition of the present invention in the other types of elastomer compositions to convey the same beneficial effects.

In the rubber composition of the present invention, base on 100 parts by mass of a diene elastomer, the antidegradant generally is present in an amount of 0.5-5.0 parts by mass, for examples, 0.5-3.5 parts by mass, 0.5-3.0 parts by mass, 1.0-3.5 parts by mass, 1.0-3.0 parts by mass, 2.0-3.5 parts by mass, or 2.0-3.0 parts by mass.

The rubber composition of the present invention may further comprise other conventional ingredients, including without limitation to, fillers, aids, crosslinkers, and promoters, and the amount of the fillers, aids, crosslinkers, and promoters may be conventionally known in the field.

Reinforcing fillers may be carbon black, titanium oxide, magnesium oxide, calcium carbonate, magnesium carbonate, aluminum hydroxide, magnesium hydroxide, clay, and talc. Generally, a reinforcing filler is used in the amount of 40-60 parts by mass per 100 parts by mass of a diene elastomer.

Aids may be softeners for improving the processability of the rubber articles. Softeners include petroleum softeners, such as processing oil, lubricant, paraffin, liquid paraffin, petroleum asphalt and vaseline; fatty oil softeners, such as castor oil, linseed oil, rapeseed oil, and coconut oil; wax, such as beewax, carnauba wax, and lanolin; tall oil; linoleic acid; palmic acid; stearic acid; and lauric acid. Aids may also be activators, such as zinc oxide, which can speed up the vulcanization rate and improve the thermal conductivity, wear resistance, and tear resistance of the rubber. Generally, aids are used at 5-15 parts by mass per 100 parts by mass of a diene rubber, for example, zinc oxide at 2-8 parts by mass and stearic acid at 1-4 parts by mass.

A crosslinker may be sulfur. Generally, the crosslinker is used in the amount of 1-3 parts by mass per 100 parts by mass of a diene elastomer.

Promoters are generally vulcanization accelerators, including at least one of sulfonamide, thiazole, thiuram, thiourea, guanidine, dithiocarbamate, aldimine, aldehyde ammonia, imidazoline, and xanthic acid vulcanization accelerators. For example, a promoter may be N-tert-butyl-2-benzothiazolesulfenamide (NS). Generally, a promoter is used in an amount of 0.5-1.5 parts by mass per 100 parts by mass of a diene elastomer.

In addition, whenever necessary, a plasticizer may be used in the rubber composition of the present invention, for examples, dimethyl phthalate (DMP), diethyl phthalate (DEP), dibutyl phthalate (DBP), diheptyl phthalate (DHP), dioctyl phthalate (DOP), di-isononyl phthalate (DINP), di-isodecyl phthalate (DIDP), butyl benzyl phthalate (BBP), dilauryl phthalate (DWP), and dicyclohexyl phthalate (DCHP). The amount of the plasticizer used is conventionally known in the art, for example, about 0.1 to 30 parts by mass per 100 parts by mass of a diene elastomer.

The rubber article of the present invention may be prepared by conventional methods such as a two-stage mixing process. In the process, the first stage mixing is performed in an internal mixer, where a diene elastomer, a reinforcing filler, an aid, and an antidegradant are blended and the rubber is discharged at 110° C. or higher, e.g., 130° C. The second stage mixing is performed in an open mill, where the mixed rubber from the first stage is blended with sulfur and a promoter, and a sheet is discharged at 110° C. or lower, e.g., 70° C. Vulcanization (curing) temperature is 130° C.-200° C., e.g., 145° C. Vulcanization time depends on the temperature, system, and dynamics of the vulcanization, and generally lasts 15-60 minutes, e.g., 30 minutes.

During the preparation process, generally, the diene elastomer is firstly added into a thermo-mechanical mixer such as an internal mixer. After kneading for a while, a reinforcing filler, an aid, and an antidegradant are added to the diene elastomer, and the mixture is kept on being kneaded until the mixture is homogeneous. The reinforcing filler, the aid, and the antidegradant may be added in batches. The temperature during kneading is controlled to between 110° C. and 190° C., and preferably between 150° C. and 160° C. Then, the mixture is cooled to 100° C. or lower. Then, a crosslinker and a promoter are added to the mixture, and a second kneading is performed during which the temperature is controlled to 110° C. or lower. Finally, vulcanization is performed, and vulcanized rubber is prepared. Optionally, the rubber composition obtained by kneading may be calendared before vulcanization.

The present invention further provides a rubber article prepared by using the rubber composition of the present invention as a rubber ingredient. For examples, the rubber article may be a tire, a rubber overshoe, a sealing strip, an acoustic panel, or a crash pad. In some embodiments of the present invention, the rubber article is a tread, a belt ply, and a sidewall of a tire. As the belt ply of the tire, the rubber article may further comprise a reinforcing material conventionally used in the art in addition to the rubber composition of the present invention. The present invention further provides a method for using the rubber composition of the present invention for preparing rubber articles or retreading tires.

The present invention further provides a method for using the antidegradant of the present invention for promoting resistance of a rubber or a rubber article to appearance discoloration. Specifically, the present invention provides a method for using the compound of Formula I for promoting resistance of a rubber or a rubber article to appearance discoloration or for preparing an antidegradant composition for promoting resistance of a rubber or a rubber article to appearance discoloration. The compound of Formula I has the following structure:

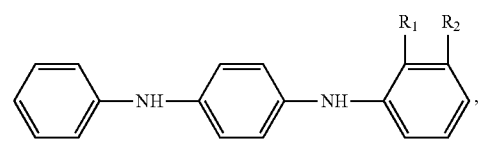

wherein $R_1$ and $R_2$ are identical or different, each being independently selected from C1-C12 alkyl and C3-C8 cycloalkyl.

In some embodiments of the present invention, $R_1$ is C1-C8 alkyl or C3-C6 cycloalkyl, and preferably C1-C6 alkyl or C3-C6 cycloalkyl. In some embodiments of the present invention, $R_1$ is methyl, ethyl, isobutyl, or cyclohexyl.

In some embodiments of the present invention, $R_2$ is C1-C12 alkyl or C3-C6 cycloalkyl. In some embodiments of the present invention, $R_2$ is methyl, ethyl, 1,3-dimethylbutyl, 1,4-dimethylamyl, octyl, 1-methyl-6-ethyloctyl, or cyclohexyl.

In some embodiments of the present invention, $R_1$ and $R_2$ are both methyl in formula I and the compound of formula I is used alone or in the antidegradant composition to promote the resistance of a rubber or a rubber article to appearance discoloration.

In some embodiments of the present invention, the rubber is natural rubber, butadiene rubber, or both.

The present invention is further illustrated in the following examples which are for illustrative purpose only and do not limit the scope of the present invention. Unless otherwise specified, the methods and materials used in the following examples are conventional in the art.

Preparation Example

A compound of Formula I of the present invention is prepared by the method disclosed in CN106608827A (corresponding to U.S. Patent Application Publication No. US2018/0237376A1 to Guo et al. published on Aug. 23, 2018) which is incorporated herein by reference in its entirety. For example, referring to Example 1 of CN106608827A, the antidegradant of the present invention where $R_1$ is methyl and $R_2$ is ethyl is prepared by reacting N-phenyl-p-phenylenediamine and 2-methyl-3-ethylcyclohexanone in presence of hydrogen acceptor, 2-methyl-3-ethylphenol, and a catalyst. The content of the product, N-(2-methyl-3-ethylphenyl)-N'-phenyl-1,4-phenylenediamine, is 78.5%, and yield is 85.8%. Antidegradants in the following examples are prepared by the same method except that different corresponding substituted cyclohexanones are used.

Example 1: Preparation of Rubber Compositions

Twelve (12) natural and butadiene rubber-based compositions marked C-1 to C-12 are prepared according to the recipes in Table 1:

TABLE 1

Recipes of Rubber Compositions (unit: parts by mass)

| Composition No. | C-1 | C-2 | C-3 | C-4 | C-5 | C-6 | C-7 | C-8 | C-9 | C-10 | C-11 | C-12 |
|---|---|---|---|---|---|---|---|---|---|---|---|---|
| NR(SCR5) | 50 | 50 | 50 | 50 | 50 | 50 | 50 | 50 | 50 | 50 | 50 | 50 |
| BR9000 | 50 | 50 | 50 | 50 | 50 | 50 | 50 | 50 | 50 | 50 | 50 | 50 |
| Black carbon N550 | 50 | 50 | 50 | 50 | 50 | 50 | 50 | 50 | 50 | 50 | 50 | 50 |
| 6PPD | 3.0 | 2.5 | 2.0 | 1.5 | 1.0 | 0.5 | 0 | 0.3 | 1.0 | 1.7 | 0 | 0 |
| IPPD | 0 | 0 | 0 | 0 | 0 | 0 | 0 | 0 | 0 | 0 | 3.0 | 1.5 |
| Antidegradant of the invention | 0 | 0.5 | 1.0 | 1.5 | 2.0 | 2.5 | 3.0 | 0.3 | 1.0 | 1.7 | 0 | 1.5 |
| Zinc oxide | 5.0 | 5.0 | 5.0 | 5.0 | 5.0 | 5.0 | 5.0 | 5.0 | 5.0 | 5.0 | 5.0 | 5.0 |
| Stearic acid | 2.0 | 2.0 | 2.0 | 2.0 | 2.0 | 2.0 | 2.0 | 2.0 | 2.0 | 2.0 | 2.0 | 2.0 |
| Sulfur | 1.5 | 1.5 | 1.5 | 1.5 | 1.5 | 1.5 | 1.5 | 1.5 | 1.5 | 1.5 | 1.5 | 1.5 |
| Promoter NS | 0.8 | 0.8 | 0.8 | 0.8 | 0.8 | 0.8 | 0.8 | 0.8 | 0.8 | 0.8 | 0.8 | 0.8 |

Rubber composition C-1 is a reference sample containing only 6PPD as the antidegradant; rubber composition C-11 is a reference sample containing only IPPD as the antidegradant; and rubber compositions C-2 to C-10 and C12 contain the antidegradants of the present invention.

In C-2, C-3, and C-12, the antidegradant of the present invention is N-(2,3-dimethylphenyl)-N'-phenyl-1,4-phenylenediamine, where both R1 and R2 are methyl as follows:

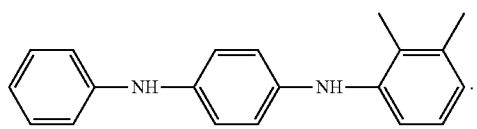 [SMILES: Cc1cccc(Nc2ccc(Nc3ccccc3)cc2)c1C]

In C-4, the antidegradant of the present invention is N-(2-methyl-3-ethylphenyl)-N'-phenyl-1,4-phenylenediamine, where R1 is methyl and R2 is ethyl as follows:

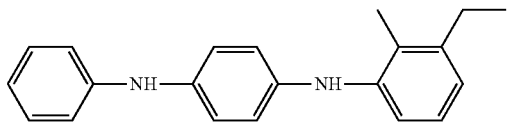

In C-5, the antidegradant of the present invention is N-(2-sec-butyl-3-cyclohexylphenyl)-N'-phenyl-1,4-phenylenediamine, where R1 is isobutyl and R2 is cyclohexyl as follows:

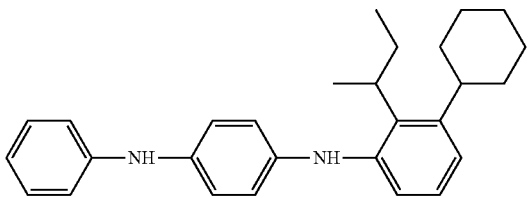

In C-6, the antidegradant of the present invention is N-[2-ethyl-3-(1,4-dimethylpentyl) phenyl]-N'-phenyl-1,4-phenylenediamine, where R1 is ethyl and R2 is 1,4-dimethylpentyl as follows:

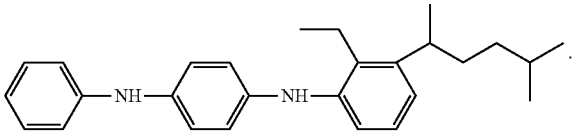 [SMILES: CCc1c(Nc2ccc(Nc3ccccc3)cc2)cccc1C(C)CCC(C)C]

In C-7, the antidegradant of the present invention is N-(2-cyclohexyl-3-octylphenyl)-N'-phenyl-1,4-phenylenediamine, where R1 is cyclohexyl and R2 is octyl as follows:

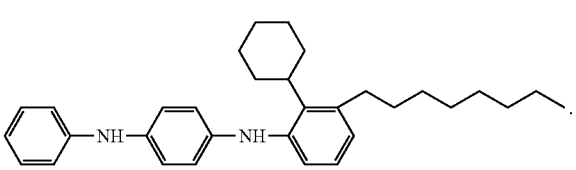 [SMILES: CCCCCCCCc1cccc(Nc2ccc(Nc3ccccc3)cc2)c1C1CCCCC1]

In C-8, the antidegradant of the present invention is N-(2-ethyl-3-cyclohexylphenyl)-N'-phenyl-1,4-phenylenediamine, where R1 is ethyl and R2 is cyclohexyl as follows:

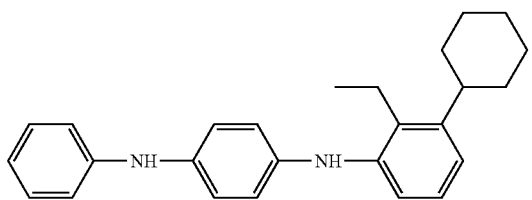

In C-9, the antidegradant of the present invention is N-[2-methyl-3-(1,3-dimethylbutyl) phenyl]-N'-phenyl-1,4-phenylenediamine, where R1 is methyl and R2 is 1,3-dimethylbutyl as follows:

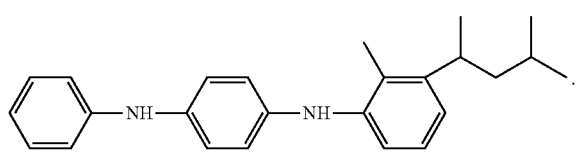 [SMILES: Cc1c(Nc2ccc(Nc3ccccc3)cc2)cccc1C(C)CC(C)C]

In C-10, the antidegradant of the present invention is N-[2-methyl-3-(1-methyl-6-ethyloctyl) phenyl]-N'-phenyl-1,4-phenylenediamine, where R1 is methyl and R2 is 1-methyl-6-ethyloctyl as follows:

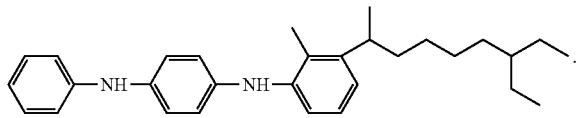 [SMILES: CCC(CC)CCCCC(C)c1cccc(Nc2ccc(Nc3ccccc3)cc2)c1C]

All rubber compositions are prepared by the following steps:
1. Diene elastomers (nature rubber NR and butadiene rubber BR9000) are added to an internal mixer for initial kneading. After kneading for a while, reinforcing filler (carbon black N550), aids (ZnO and stearic acid), and antidegradants (6PPD, IPPD, antidegradant of the present invention, or combination thereof) are added in batches, and kneading is kept on until the mixture is homogeneous while controlling the temperature at between 150° C. and 160° C.
2. The whole mixture is cooled to 100° C. or lower, then, a crosslinking system (sulfur and a promoter NS) is added, followed by kneading the whole mixture while controlling the temperature at 110° C. or lower.
3. The rubble composition obtained is calendered into a form of sheet (2-3 mm in thickness), and the physicochemical properties before vulcanization are measured.
4. The rubble composition is vulcanized at 145° C. for 30 minutes. Mechanical and aging properties of the rubber composition after the vulcanization are measured.

Example 2: Testing Rubber Properties

Properties of the rubber compositions in Example 1 are measured before vulcanization according to GB/T 16584-1996 "Rubber—Measurement of Vulcanization Characteristics With Rotorless Curemeters." Vulcanized rubbers prepared in Example 1 are tested for hot air aging test according to GB/T 3512-2014 "Rubber, vulcanized or thermoplastic—accelerated aging and heat resistance tests—air oven method." Test results on properties of the rubber compositions before vulcanization and vulcanized rubbers before and after aging are shown in Table 2:

TABLE 2

| Test Results on Rubber Properties | | | | | | | | | | | | |
|---|---|---|---|---|---|---|---|---|---|---|---|---|
| Composition No. | C-1 | C-2 | C-3 | C-4 | C-5 | C-6 | C-7 | C-8 | C-9 | C-10 | C-11 | C-12 |
| Properties before vulcanization | | | | | | | | | | | | |
| t10 (min) | 7.12 | 7.01 | 6.89 | 7.65 | 7.34 | 7.44 | 7.76 | 8.02 | 7.94 | 7.54 | 7.38 | 7.24 |
| t90 (min) | 13.96 | 14.22 | 14.09 | 15.39 | 14.68 | 14.52 | 15.32 | 15.54 | 15.41 | 14.67 | 14.38 | 15.01 |
| Properties after vulcanization before aging | | | | | | | | | | | | |
| MA100 (MPa) | 2.1 | 2.3 | 2.2 | 2.2 | 2.3 | 2.3 | 2.2 | 2.2 | 2.2 | 2.2 | 2.3 | 2.2 |
| MA300 (MPa) | 9.3 | 9.8 | 9.8 | 9.7 | 9.6 | 9.8 | 9.7 | 9.8 | 9.7 | 9.6 | 9.5 | 9.6 |
| Elongation at break % | 476 | 440 | 443 | 456 | 465 | 456 | 463 | 454 | 452 | 468 | 455 | 461 |
| Tensile strength (MPa) | 17.4 | 16.8 | 17.0 | 17.3 | 17.5 | 16.9 | 17.8 | 17.2 | 16.8 | 17.3 | 17.1 | 17.7 |
| Properties after vulcanization and after aging (100° C., 72 hours) | | | | | | | | | | | | |
| Elongation at break % | 387 | 376 | 365 | 393 | 377 | 384 | 395 | 357 | 360 | 387 | 366 | 361 |
| Tensile strength (MPa) | 15.0 | 15.2 | 15.0 | 15.6 | 15.1 | 15.3 | 15.8 | 14.7 | 14.9 | 15.4 | 15.1 | 15.0 |

Example 2 shows that the mechanical properties of rubber compositions prepared using the antidegradants of the present invention, either alone or combined with 6PPD or IPPD, are similar to those of the reference samples.

Examples 3: Ozone Testing

Vulcanized rubbers prepared in Example 1 are subjected to static and dynamic ozone resistance testing in an ozone aging test chamber according to GB/T 11206-2003 "Standard Test Method for Rubber Deterioration—Surface Cracking" and GB/T 13642-2015 "Rubber, Vulcanized or Thermoplastic—Resistance to Ozone Cracking—Dynamic Strain Testing." Concentration by volume of ozone is 50 pphm, temperature is (40±2°) C., and humidity is (50±5)%.
In the static testing, samples are stretched and elongated to certain length and maintained at the length, which mimics the tires or other rubber products that would have ozone cracking under static deformation. In the test, the elongation is 20% and the testing is run continuously for 72 hours. Samples are observed for cracking, and the results are shown in Table 3:

TABLE 3

Static Testing Result

| Composition | C-1 | C-2 | C-3 | C-4 | C-5 | C-6 | C-7 | C-8 | C-9 | C-10 | C-11 | C-12 |
|---|---|---|---|---|---|---|---|---|---|---|---|---|
| Cracking | No | No | No | No | No | Slight | Slight | Slight | Slight | No | Slight | Slight |

In the dynamic testing, samples are continuously stretched and elongated and released and relaxed, which mimics the tires during operation or other rubber products that undergo ozone cracking under the dynamic conditions. In the test, the elongation is 10%, the frequency is 0.5 Hz, and the testing is run continuously for 72 hours. Samples are observed for cracking, and the results are shown in Table 4:

TABLE 4

Dynamic Testing Results

| Composition | C-1 | C-2 | C-3 | C-4 | C-5 | C-6 | C-7 | C-8 | C-9 | C-10 | C-11 | C-12 |
|---|---|---|---|---|---|---|---|---|---|---|---|---|
| Cracking | No | No | No | No | Slight | Slight | Slight | Slight | Slight | No | Slight | Slight |

In Tables 3 and 4, "Slight" refers to the crack width that is 0.1 mm or less and the crack density is 10 cracks per cm or less. Slight cracks are hard to distinguish by the naked eye and do not affect actual use and appearance.

Example 3 shows that under the static ozone cracking test, compositions C-1 to C-5 and C-10 have no cracking, while compositions C-6 to C-9, C-11, and C-12 have slight cracking, which are various in degree and minor fine cracking. Under the dynamic ozone cracking test, compositions C-1 to C-4 and C-10 have no cracking, while compositions C-5 to C-9, C-11, and C-12 have slight cracking, which are various in degree and minor fine cracking. Therefore, all the compositions exhibit good to excellent static anti-ozone cracking property that mirror the dynamic anti-ozone cracking property except that composition C-5 has the dynamic anti-ozone cracking property that is not as good as its static anti-ozone cracking property.

Example 4: UV and Weathering Testing

Vulcanized rubbers prepared in Example 1 are subjected to UV-aging testing according to GB/T 16585-1996 "Rubber, Vulcanized—Test Method of Resistance to Artificial weathering (Fluorescent UV lamp)." UV lamp model is UVA, wavelength is 340 nm, irradiance is 0.98 W/m$^2$, and experimental temperature is 60° C. Cycles of UV exposure for 4 hours and condensation for 4 hours are adopted and samples observed every 72 hours. Total exposure time is 288 hours and discoloration on surface of samples is observed. Results are shown in Table 5:

TABLE 5

UV Testing Results

| Composition | C-1 | C-2 | C-3 | C-4 | C-5 | C-6 | C-7 | C-8 | C-9 | C-10 | C-11 | C-12 |
|---|---|---|---|---|---|---|---|---|---|---|---|---|
| Discoloration | 4 | 1 | 1 | 0 | 0 | 0 | 0 | 0 | 0 | 1 | 4 | 1 |

Weathering testing is to place vulcanized rubbers prepared in Example 1 in the open air. Observation is conducted every 7 days for a total of 49 days, and discoloration of the surface is observed. Results are shown in Table 6:

TABLE 6

Weathering Testing Results

| Composition | C-1 | C-2 | C-3 | C-4 | C-5 | C-6 | C-7 | C-8 | C-9 | C-10 | C-11 | C-12 |
|---|---|---|---|---|---|---|---|---|---|---|---|---|
| Discoloration | 4 | 1 | 1 | 0 | 0 | 0 | 0 | 0 | 0 | 1 | 4 | 1 |

The discoloration level is described in Table 7:

TABLE 7

Description of Discoloration Level

| Level | Description |
|---|---|
| 0 | No color change |
| 1 | Slight discoloration of small area, which can be found only by careful comparison |
| 2 | Slight discoloration of large or all area, which can be easily found after comparison |
| 3 | Serious discoloration of small area, which can be directly found |
| 4 | Serious discoloration of large or all area, which can be directly found |

Example 4 shows that, compared to reference rubber compositions prepared by using 6PPD or IPPD only, rubber compositions using the antidegradants of the present invention alone or in combination with 6PPD or IPPD possess better resistance to appearance discoloration.

We claim:

1. A compound of Formula I:

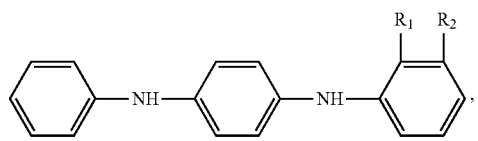

wherein the compound of Formula I is a N-phenyl-N'-(2,3-disubstituted phenyl)-p-phenylenediamine, $R_1$ and $R_2$ are identical or different, each being independently selected from C1-C12 alkyl and C3-C8 cycloalkyl; and $R_1$ and $R_2$ are not methyl at the same time.

2. The compound of claim 1, wherein $R_1$ is C1-C6 alkyl or C3-C6 cycloalkyl.

3. The compound o claim 1, wherein $R_1$ is methyl, ethyl, isobutyl, or cyclohexyl.

4. The compound of claim 1, wherein $R_2$ is C1-C12 alkyl or C3-C6 cycloalkyl.

5. The compound of claim 1, wherein $R_2$ is methyl, ethyl, 1,3-dimethylbutyl, 1,4-dimethylamyl, octyl, 1-methyl-6-ethyloctyl, or cyclohexyl.

6. A rubber composition comprising the compound of claim 1.

7. The rubber composition of claim 6, wherein the compound is present in an amount of 0.5-5.0 parts by mass based on 100 parts by mass as a content of the diene elastomer comprised in the rubber composition.

8. A rubber article prepared using the rubber composition of claim 6 as rubber ingredient.

9. The rubber article of claim 8, wherein the rubber article is a tire, a rubber overshoe, a sealing strip, an acoustic panel, or a crash pad.

10. A method for using the rubber composition of claim 6, comprising
preparing a rubber article or retreading tires by using the rubber composition of claim 6.

11. The compound of Formula I as described in claim 1, wherein $R_1$ and $R_2$ are selected from the group consisting of when $R_1$ is methyl, $R_2$ is ethyl, 1,3-dimethylbutyl, or 1-methyl-6-ethyloctyl; when $R_1$ is ethyl, $R_2$ is 1,4-dimethylamyl or cyclohexyl; when $R_1$ is isobutyl, $R_2$ is cyclohexyl; and when $R_1$ is cyclohexyl, $R_2$ is octyl.

12. An antidegradant composition comprising a first compound of Formula I:

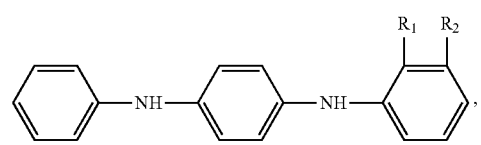

wherein $R_1$ and $R_2$ are identical or different, each being independently selected from C1-C12 alkyl and C3-C8 cycloalkyl, and
a second antidegradant that is not the first compound of Formula I; and $R_1$ and $R_2$ are not methyl at same time.

13. The antidegradant composition of claim 12, wherein the second antidegradant is a pollution-type antidegradant.

14. The antidegradant composition of claim 12, wherein the second antidegradant is 6PPD, IPPD, or both.

15. The antidegradant composition of claim 12, wherein mass ratio of the first compound to the second antidegradant is in a range of 1:6 to 6:1.

16. The antidegradant composition of claim 12, wherein R1 is C1-C6 alkyl or C3-C6 cycloalkyl.

17. The antidegradant composition of claim 12, wherein R2 is C1-C12 alkyl or C3-C6 cycloalkyl.

18. The antidegradant composition of claim 12, wherein R1 is methyl, ethyl, isobutyl, or cyclohexyl.

19. The antidegradant composition of claim 12, wherein R2 is methyl, ethyl, 1,3-dimethylbutyl, 1,4-dimethylamyl, octyl, 1-methyl-6-ethyloctyl, or cyclohexyl.

20. A rubber composition comprising the antidegradant composition of claim 12.

21. A method for promoting resistance of a rubber or a rubber article to appearance discoloration, comprising
using a compound of Formula I in a rubber or rubber article:

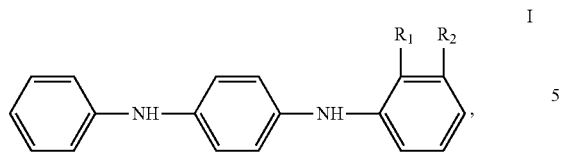
wherein $R_1$ and $R_2$ are identical or different, each being independently selected from C1-C12 alkyl and C3-C8 cycloalkyl; and $R_1$ and $R_2$ are not methyl at same time.
* * * * *